(12) United States Patent
DiRisio

(10) Patent No.: US 11,272,893 B2
(45) Date of Patent: Mar. 15, 2022

(54) COLLAPSIBLE COLUMN MOVEMENT APPARATUS FOR MOBILE X-RAY DEVICE

(71) Applicant: CARESTREAM HEALTH, INC., Rochester, NY (US)

(72) Inventor: Anthony DiRisio, Rochester, NY (US)

(73) Assignee: Carestream Health, Inc., Rochester, NY (US)

( * ) Notice: Subject to any disclaimer, the term of this patent is extended or adjusted under 35 U.S.C. 154(b) by 0 days.

(21) Appl. No.: 16/923,378

(22) Filed: Jul. 8, 2020

(65) Prior Publication Data

US 2021/0007686 A1 Jan. 14, 2021

Related U.S. Application Data

(60) Provisional application No. 62/871,746, filed on Jul. 9, 2019.

(51) Int. Cl.
*A61B 6/00* (2006.01)

(52) U.S. Cl.
CPC ............ *A61B 6/4405* (2013.01); *A61B 6/447* (2013.01); *A61B 6/4452* (2013.01)

(58) Field of Classification Search
CPC ...... A61B 6/4405; A61B 6/4452; A61B 6/447
See application file for complete search history.

(56) References Cited

U.S. PATENT DOCUMENTS

| | | |
|---|---|---|
| 2,041,242 A | 5/1936 | Goldfield |
| 3,790,805 A | 2/1974 | Foderaro |
| 4,341,279 A | 7/1982 | Waerve |
| 4,387,468 A | 6/1983 | Fenne et al. |
| 4,716,581 A | 12/1987 | Barud |
| 4,989,229 A | 1/1991 | Negrelli et al. |
| 5,067,145 A | 11/1991 | Siczek et al. |
| 5,388,142 A | 2/1995 | Morris |
| 5,425,069 A | 6/1995 | Pellegrino et al. |
| 5,475,730 A | 12/1995 | Galando |
| 5,499,284 A | 3/1996 | Pellegrino et al. |
| 5,544,217 A | 8/1996 | Kadowaki et al. |
| 5,844,961 A | 12/1998 | McEvoy et al. |
| 6,193,415 B1 | 2/2001 | Kadowaki et al. |
| 6,217,214 B1 | 4/2001 | Cabral et al. |
| 6,237,707 B1 | 5/2001 | Lyke et al. |
| 6,491,430 B1 | 12/2002 | Scissler |

(Continued)

FOREIGN PATENT DOCUMENTS

| | | |
|---|---|---|
| CN | 1665448 | 9/2005 |
| CN | 101601587 | 12/2009 |

(Continued)

OTHER PUBLICATIONS

International Search Report & Written Opinion, International application No. PCT/US2011/032030, dated Dec. 19, 2011, 2 pages.

(Continued)

*Primary Examiner* — Chih-Cheng Kao

(57) ABSTRACT

A mobile radiography system with a wheeled transport frame has a vertical column mounted on the transport frame to hold in position an x-ray tube head. One or more pulley systems inside the vertical column and/or the transport frame allow easily manually adjusting a height of the x-ray tube head. The pulley systems may include cables and fixed and movable pulleys.

19 Claims, 5 Drawing Sheets

(56) References Cited

U.S. PATENT DOCUMENTS

| | | |
|---|---|---|
| 6,851,853 B2 | 2/2005 | Nakagawa et al. |
| 7,016,467 B2 | 3/2006 | Brooks |
| 7,211,802 B1 | 5/2007 | Dhurjaty et al. |
| 7,495,226 B2 | 2/2009 | Jadrich et al. |
| 7,611,282 B2 | 11/2009 | Koren et al. |
| 8,568,028 B2 | 10/2013 | Wendlandt et al. |
| 8,672,543 B2 | 3/2014 | Kralles et al. |
| 8,876,379 B2 | 11/2014 | DiRisio et al. |
| 11,051,775 B2 * | 7/2021 | Dirisio .................. A61B 6/545 |
| 2003/0190014 A1 | 10/2003 | Nakagawa et al. |
| 2011/0249804 A1 | 10/2011 | Wendlandt et al. |
| 2011/0249806 A1 | 10/2011 | Wendland et al. |
| 2011/0249807 A1 | 10/2011 | Dirisio et al. |
| 2016/0199013 A1 * | 7/2016 | Moreno Vallejo ..... A61B 6/447 378/194 |

FOREIGN PATENT DOCUMENTS

| | | |
|---|---|---|
| CN | 101601588 | 12/2009 |
| CN | 101601589 | 12/2009 |
| GB | 1224814 | 3/1971 |
| JP | 59-036200 U | 7/1984 |
| JP | 04-164437 | 6/1992 |
| JP | 04-276238 | 10/1992 |
| JP | 2003-052689 | 2/2003 |
| JP | 2004-033415 | 2/2004 |
| JP | 2004-113326 | 4/2004 |
| JP | 2004-121405 | 4/2004 |
| JP | 2004-121407 | 4/2004 |
| JP | 2005-013490 | 1/2005 |
| JP | 2005-073710 | 3/2005 |
| JP | 2006-068487 | 3/2006 |
| JP | 2008-173256 | 7/2008 |
| WO | 90-14748 | 11/1990 |
| WO | 2004/004568 | 1/2004 |

OTHER PUBLICATIONS

International Search Report & Written Opinion, International application No. PCT/US2011/032041, dated Dec. 12, 2011, 2 pages.
International Search Report & Written Opinion, International application No. PCT/US2011/032026, dated Dec. 12, 2011, 2pages.
Supplementary European Search Report for European Patent Application No. 11 769 399.4, completed Feb. 26, 2014, 2 Pages.
Supplementary European Search Report for European Patent Application No. 11 769 407.5, completed Feb. 25, 2014, 2 Pages.

* cited by examiner

COLLAPSIBLE COLUMN MOVEMENT APPARATUS FOR MOBILE X-RAY DEVICE

CROSS REFERENCE TO RELATED APPLICATIONS

This application claims priority to U.S. Patent Application Ser. No. 62/871,746, filed Jul. 9, 2019, in the name of Anthony DiRisio, and entitled COLLAPSIBLE COLUMN MOVEMENT APPARATUS FOR MOBILE X-RAY DEVICE, which is hereby incorporated by reference herein in its entirety.

This application is related in certain respects to U.S. Pat. No. 8,568,028, filed Oct. 18, 2010, in the name of Wendlandt et al., and entitled Mobile radiography unit having collapsible support column; U.S. Pat. No. 8,672,543, filed Apr. 11, 2011, in the name of Kralles et al., and entitled Counterweight for mobile x-ray device; and U.S. Pat. No. 8,876,379, filed Apr. 11, 2011, in the name of DiRisio et al., and entitled Collapsible column movement apparatus for mobile x-ray device; all of which are hereby incorporated by reference herein in their entirety.

FIELD OF THE INVENTION

The present invention relates generally to the field of radiography and in particular to portable radiographic imaging apparatus. More specifically, the invention relates to column height adjustment in a mobile radiography apparatus having a collapsible support column with an x-ray boom of adjustable height.

BACKGROUND OF THE INVENTION

Mobile x-ray apparatus are of particular value in intensive care unit (ICU) and other environments where timely acquisition of a radiographic image is important. Because it can be wheeled around the ICU or other area and brought directly to the patient's bedside, a mobile x-ray apparatus allows an attending physician or clinician to obtain diagnostic information on the condition of a patient and helps to reduce the risks entailed in moving patients to stationary x-ray equipment in the radiological facility.

The perspective view of FIG. 1 shows an example of a conventional mobile x-ray or radiography apparatus 20 that can be employed for computed radiography (CR) and/or digital radiography (DR). The mobile radiography apparatus 20 has a transport frame 22 that may include a display for obtained x-ray images and related data and a control panel including a keyboard that allows instruction entry for storing, transmitting, modifying, and printing of the obtained x-ray images.

For mobility, radiography apparatus 20 has wheels 10 and one or more handle grips 12 typically provided at waist-, arm-, or hand-level, that help to move radiography apparatus 20 to its intended location. A self-contained battery pack typically provides source power, eliminating the need for operation near a power outlet.

Mounted to transport frame 22 is a column 30 having a vertically stationary base section 32 and a movable section 36 that is movable parallel to, and relative to, vertically stationary base section 32 along a vertical axis V. Column 30 has a boom transport mechanism 40 that moves, or slides, relative to movable section 36 vertically along a track 42 in movable section 36. Attached to the boom transport mechanism 40 is a telescoping boom 70 which supports a tube head attached to an end of the boom 70, which tube head contains an x-ray source 68. Boom 70 extends outward a variable distance from column 30 along horizontal axis H and translates up and down manually to a desired height for obtaining an x-ray image using x-ray source 68. Height settings for the x-ray source 68 can range from low height for imaging feet and lower extremities to shoulder height and above for imaging the upper body portions of patients in various positions. In other conventional embodiments, the column 30 is not a linear vertical column, but is rather an articulated member that bends at an elbow joint to allow movement of the x-ray source over a range of vertical and horizontal positions. FIG. 2 illustrates the radiography apparatus 20 in a docked configuration, suitable for the radiography apparatus 20 to be wheeled to an intended location, whereby the base section 32 and movable section 36 are rotated about vertical axis V and movable section 36 is lowered into base section 32.

One concern that must be addressed in design of the mobile radiography apparatus 20 relates to ease of positioning of the x-ray source 68 mounted on its boom 70. For ease of operation under varying conditions, the technician should be able to easily position and orient the x-ray source without requiring both hands, without the need of additional tools, and without needing help from nearby personnel. This includes moving the x-ray source from its docked position used in transport to an imaging position. The mechanical problem of providing ease of positioning is complicated by the weight of the x-ray source and by its extension outward from the vertical axis V. Boom 70 that provides transport of x-ray source 68, normally extended outward when in its imaging position, is folded back for transport. This transport position helps to protect the x-ray source 68 from damage or from causing an obstruction during movement.

While the collapsible column 30 has advantages over fixed columns, however, a number of problems remain to be solved. One area of particular interest relates to boom movement for height adjustment. Because both the column height and boom height are adjustable, some amount of coordination is useful to help make it more natural to switch between various height positions, preferably so that the technician can concentrate attention on obtaining the best setup conditions for exposure without excessive concern for setting or adjusting column height relative to boom height.

Thus, there is a need for improvements in mobile x-ray apparatus design that allow ease of height adjustment of a collapsible column relative to the height of its boom transport mechanism.

BRIEF DESCRIPTION OF THE INVENTION

An object of the present invention is to advance the art of mobile radiography. Another object of the present invention is to address the need for a mobile radiography unit that allows ease of movement of the boom assembly between vertical positions.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

In one embodiment, the present invention can provide a mobile radiography apparatus comprising: a portable transport frame; a sectioned vertical column mounted on the frame and defining a vertical axis and comprising a base section having a first vertical position relative to the vertical axis and at least one movable section that is translatable to a variable vertical position along the vertical axis; a counterweight apparatus coupled to the at least one movable section of the vertical column; a boom supporting an x-ray source and coupled to the at least one movable section for vertical displacement of the boom to a height position. One or more column cables and pulley systems, including the counterweight apparatus, comprises a column cable having a first end attached to the boom and a second end attached to the base section, which cable and pulley system mechanically assists a user to adjust a height of the boom and x-ray source.

In one embodiment, the present invention can provide a mobile radiography apparatus comprising a portable transport frame; a sectioned vertical column mounted on the frame and defining a vertical axis and comprising a base section having a fixed vertical position relative to the vertical axis and a movable section that is translatable to a variable vertical position along the vertical axis, a counterbalance apparatus coupled to the movable section of the vertical column, and comprising a tension force adjustment element in the transport frame. A boom apparatus supports an x-ray source and is movably coupled to the movable section for vertical displacement of the boom apparatus to a height position within a range of height positions along the movable section. One or more cable and pulley systems within the vertical column and/or the transport frame interacts with the counterbalance apparatus to mechanically assist a user to adjust a height of the boom apparatus and x-ray source.

In one embodiment, the present invention can provide a method for setting up a portable radiographic unit for an exposure, comprising mounting a sectioned vertical column on a portable transport frame, wherein the column defines a vertical axis and comprises a base section having a first vertical position relative to the vertical axis and at least one movable section that is vertically translatable to extend the vertical column along the vertical axis; coupling a boom apparatus supporting an x-ray source to the at least one movable section for vertical displacement of the boom apparatus to a height position; and responding to an operator urging to adjust the height of the boom apparatus for the exposure by translating at least the boom apparatus and, in certain instances, the movable section along the vertical axis. One or more cable and pulley systems within the vertical column and/or the portable transport frame mechanically assist a user to adjust a height of the boom and x-ray source.

In another embodiment, the present invention can provide a method for setting up a portable radiographic unit for an exposure, comprising providing a sectioned vertical column mounted on a portable transport frame, wherein the column defines a vertical axis and comprises a base section having a fixed vertical position relative to the vertical axis and a movable section that is translatable to a variable vertical position along the vertical axis; coupling a boom apparatus supporting an x-ray source to the movable section for vertical displacement of the boom apparatus to a height position, wherein the boom apparatus is movably displaceable vertically over a range that extends along at least a portion of the movable section. One or more cable and pulley systems within the vertical column and/or the portable transport frame mechanically assist a user to adjust a height of the boom and x-ray source.

In another embodiment, a mobile radiography system includes a transport frame having wheels for rolling the system to a patient bedside. A transport frame housing encloses at least a portion of the system. A sectioned vertical column is mounted on the rollable transport frame and includes a base section supported by and attached to the transport frame, which base section is rotatable, relative to the transport frame, about a vertical axis while remaining vertically stationary with respect to the transport frame. A movable upper section of the vertical column is coupled to the base section and is movable parallel to the vertical axis and relative to the base section. A boom having a first end attached to the movable upper section, and extending transversely therefrom, includes an x-ray source attached to a second end opposite the first end. The boom is configured to move as a unit vertically along a length of the movable upper section. One or more cable and pulley systems within the sectioned vertical column and/or within the transport frame assist a user to adjust a height of the boom and the x-ray source attached thereto.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which.

DETAILED DESCRIPTION OF THE INVENTION

Apparatus and methods of the present invention address the need for a radiography unit that can be readily rolled from one place to another within a treatment facility, without the physical or visual obstruction that is common to many types of conventional mobile radiography equipment that use a vertical column. As noted previously, the x-ray source of such a system must allow elevation over a wide vertical range of motion, from heights near or above shoulder level for adults to very low elevations near the ankle or foot. One way to achieve this range of movement is the use of a jointed support member, as described previously. A somewhat simpler mechanical design is the use of a vertical column as was shown in FIGS. 1 and 2, with the x-ray source mounted on a boom that extends outward horizontally from the column and travels vertically up and down the column. Two degrees of freedom are needed for boom 70 movement relative to the vertical column: translation along the vertical direction, that is, along the vertical axis, and rotation about the vertical axis. Boom 70 typically also extends to a variable horizontal length in a direction H relative to the vertical axis, although it should be noted that a boom of fixed length could be used in a mobile radiography apparatus of the present invention.

Figure 1:
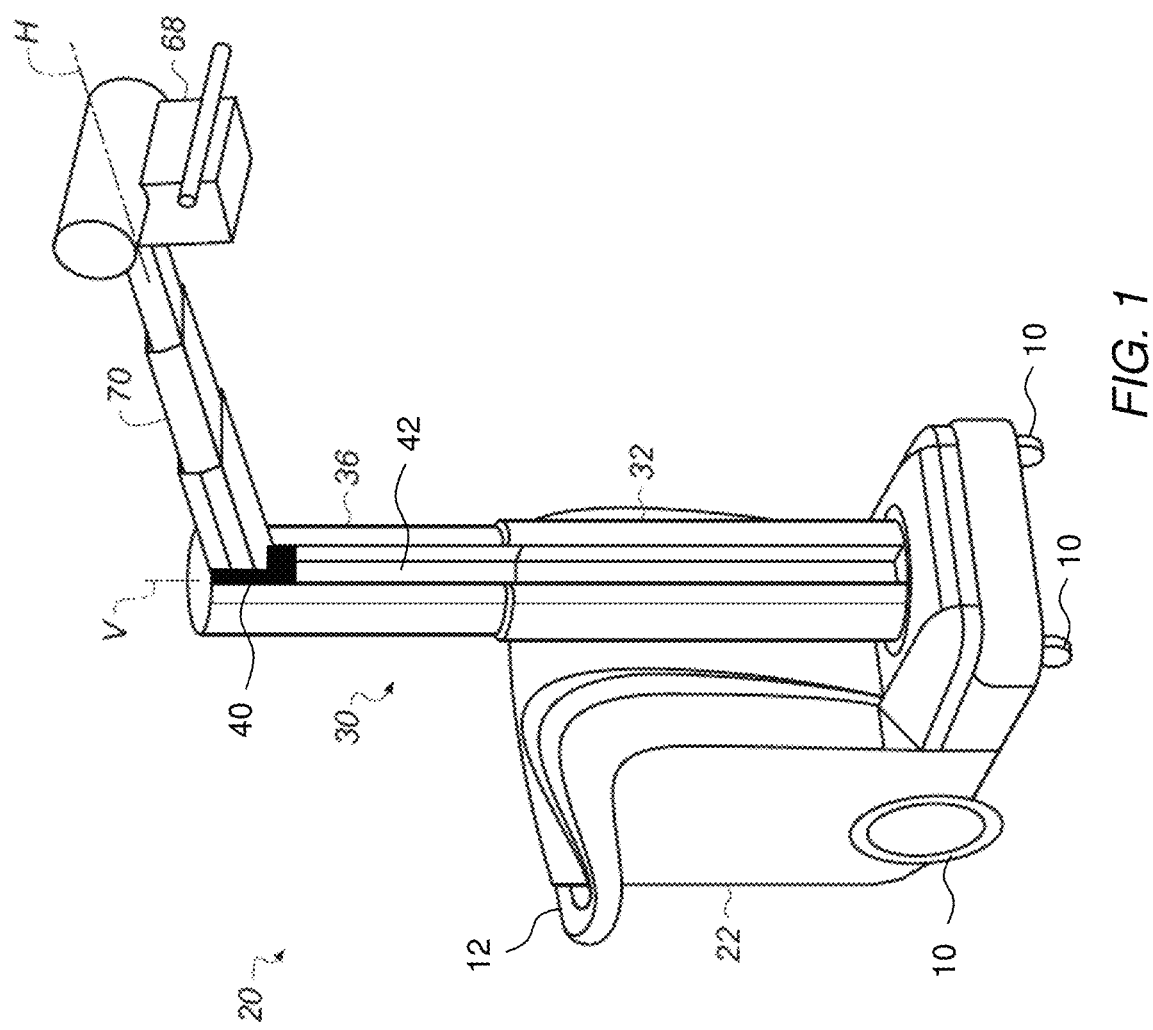
FIG. 1 shows a perspective view of a mobile radiography apparatus with a sectioned vertical column according to one embodiment of the present invention.
Figure 2:
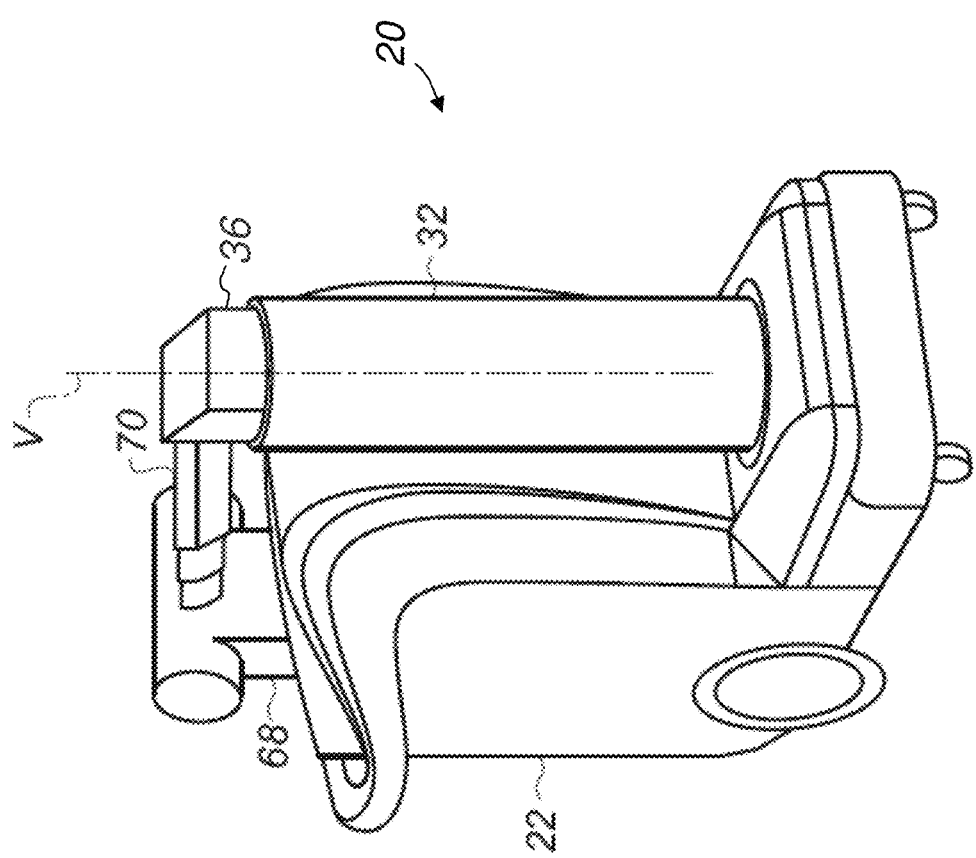
FIG. 2 shows a perspective view of the mobile radiography apparatus configured for travel.

The perspective view of FIG. 1 shows a mobile radiography unit 20 that has boom 70 coupled to a sectioned vertical column 30. According to one embodiment, sectioned vertical column 30 includes a movable section 36 telescopically extendable out of, and into, stationary base section 32, which is rotatably attached to transport frame 22. FIG. 1 shows unit 20 with x-ray source 68 in position for imaging, extended outward and supported on boom 70, along a horizontal axis H that is perpendicular to the vertical axis V. FIG. 2 shows unit 20 in an alternate arrangement, configured for travel, with the sectioned vertical column collapsed by lowering movable section 36 into stationary section 32 and with x-ray source 68 nestled against a top surface of the transport frame 22. In each of these embodiments, both rotation about vertical axis V and vertical displacement along the vertical axis can be performed simultaneously. In the travel configuration of FIG. 2, sectioned vertical column 30 is collapsed and boom 70 is rotated inward in order to seat x-ray source 68 in a stable, docked position for movement, such as for wheeling the entire mobile radiography unit 20 from one patient area to another.

Embodiments of the present invention address this difficulty by using a boom transport mechanism 40 that cooperates mechanically with a telescoping, sectioned vertical column 30 to allow displacement of the x-ray boom over a wide range of height settings. Advantageously, the operator can easily adjust x-ray boom height, with the weight of column and boom components mechanically balanced so that a substantially uniform amount of effort is needed for height adjustment to any level within the height range.

Figure 3:
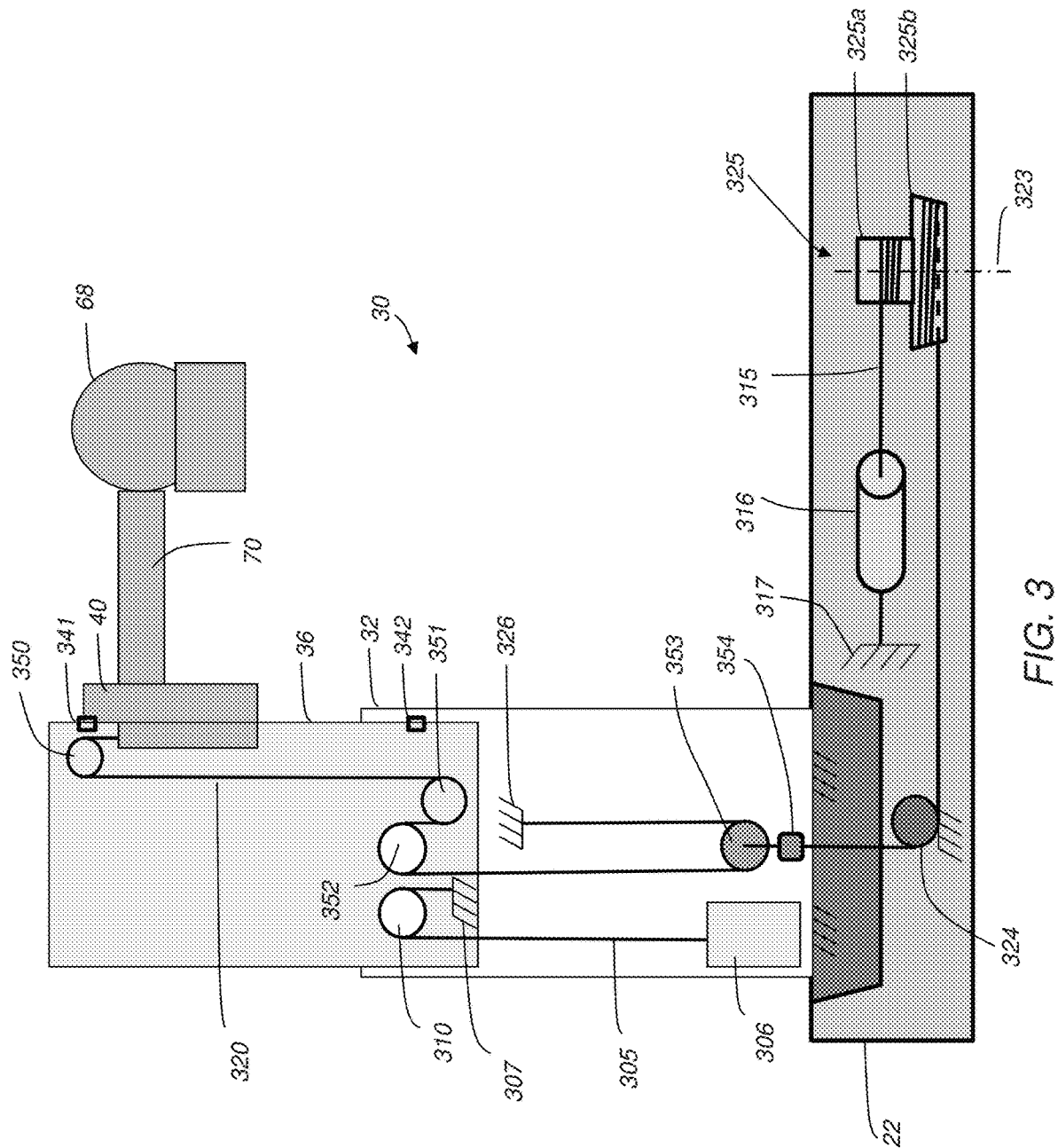
FIG. 3 is a schematic block diagram of a boom apparatus on a portion of a sectioned vertical column using a novel assembly of cables, pulleys, and spring to assist vertical positioning.

FIG. 3 is a schematic diagram of a vertical movement mechanical assist assembly disposed within the vertical column sections 32, 36, and within a housing of the transport frame 22. The wheels 10 attached to transport frame 22 are not shown for ease of illustration. The vertical movement mechanical assist assembly may include up to three cable and pulley systems as described herein, including movable and fixed pulley cable systems and a tension adjustment element, such as a spring. A first cable and pulley system uses a cable 320 having one end attached to the boom transport mechanism 40, and an opposite end attached, or anchored, to the base section 32 of the vertical column 30 at a cable ground, or anchor point, 326 affixed on an interior surface thereof. The fixed and movable pulleys as described herein may have an annular groove along a circumference of a rotatable wheel to guide a cable, belt, chain or rope looping around the pulleys. The wheel and groove portion of the fixed pulleys described herein rotate about a fixed stationary center shaft coinciding with a central rotational axis of the fixed pulleys. These center shafts of the fixed pulleys may be attached to a part of the vertical column 30 or transport frame 22, allowing the wheel of the pulleys to rotate around a fixed axis.

As shown in FIG. 3, the cable 320 extends upward from its attachment to the boom transport mechanism 40 then loops downward around fixed pulley 350, attached by its central shaft to the movable column section 36 on an interior surface thereof, then loops upward around fixed pulley 351, also attached by its central shaft to the movable column section 36 on an interior surface thereof, then loops downward around fixed pulley 352, attached by its central shaft to the base column section 32 on an interior surface thereof, and then loops upward around movable floating pulley 353 to the cable 320 anchor point 326, affixed on an interior surface of the base section 32 of vertical column 30, as shown in FIG. 3. The first cable and pulley system just described may be said to be disposed within the vertical column 30 of the mobile radiography apparatus.

A second cable and pulley system, cooperating with the first cable and pulley system, uses a cable 315 having one end attached to the floating and movable pulley 353, and an opposite end attached, or anchored, to the transport frame 22 at a cable ground, or anchor point, 317 affixed to an interior surface thereof. The cable 315 travels downward from the movable floating pulley 353 into the transport frame 22, then loops transversely outward further into transport frame 22, at an angle of about 90° from its downward portion, around fixed pulley 324 attached by its central shaft to a fixed interior portion of the transport frame 22. Cable 315 then loops around a tapered wide portion 325b of a dual radius fixed pulley 325 attached by its central shaft to the transport frame section 22 on an interior surface thereof. Then the cable 315 extends from the tapered dual radius fixed pulley 325 in an opposite direction (180°) back toward one end of a tension adjustment member 316, such as a spring, to which the cable 315 is attached. Another section of cable 315 is attached to a second end of tension adjustment member 316 and then to the cable 315 anchor point 317 affixed on an interior surface of the transport frame 22, as shown in FIG. 3.

The tapered dual radius fixed pulley 325 comprises a smaller radius portion 325a whereabout the cable 315 loops one or more times and continues to the adjustable tension member 316. The tapered dual radius fixed pulley 325 comprises a wider radius tapered portion 325b whereabout the cable 315 loops one or more times and continues to the fixed pulley 324. The wider radius tapered portion 325b of the tapered dual radius fixed pulley 325 comprises a tapered radius portion that provides a continuously variable radius for the cable 315 that loops around it. The larger portion of wider radius tapered portion 325b is adjacent the smaller radius portion 325a as compared to the smaller portion of 325b. The smallest radius of the wider radius tapered portion 325b of the dual radius fixed pulley 325 may be greater than the radius of the smaller radius portion 325a of the dual radius fixed pulley 325. The dual radius fixed pulley 325 may be configured to guide a single continuous cable 315 or, in an alternative embodiment, two cable sections of the cable 315. In a two cable section embodiment, a section of cable 315 that extends to fixed pulley 324, may loop around one or more times and be anchored to the larger tapered radius portion 325b of the fixed dual radius pulley 325, and a second separate section of cable 315 may extend from the adjustable tension member 316 and loop around one or more times and be anchored to the smaller radius portion 325a of the fixed dual radius pulley 325. In a single cable embodiment, one continuous cable 315 loops around both the smaller and larger radius portions 325a, 325b, of the dual radius fixed pulley 325. The single cable embodiment typically requires the cable 315 to be clamped, or anchored, to the dual radius fixed pulley 325 at a selected location between the two pulley radius portions 325a, 325b. The second cable and pulley system just described may be said to be disposed within the transport frame 22 of the mobile radiography apparatus, except for the portion of cable 315 that travels into the base section 32 for attachment to the movable floating pulley 353. The portions, or sections, of cable 315 described herein may be referred to as simply cable 315. The axis of rotation 323 of tapered dual radius fixed pulley 325 may be parallel to the vertical column 30.

A third cable and pulley system, cooperating with the first and second cable and pulley systems described above, uses a cable 305 having one end attached to a counterweight 306 and an opposite end attached, or anchored, to the movable column section 36 at a cable ground, or anchor point, 307 affixed thereto. The cable 305 travels upward from the counterweight 306 then loops downward around fixed pulley 310 attached by its central shaft to the base section 32 on an interior surface thereof, and then to its anchor point 307 on the movable section 36, as shown in FIG. 3. The third cable and pulley system just described may be said to be disposed within the vertical column 30 of the mobile radiography apparatus.

An alternative swivel 354 may be used to connect the cable 315 to the movable pulley 353. The swivel is connected on one side to an end of a first portion of the cable 315, and is connected on a second side to a second portion of the cable 315. The swivel 354 allows the movable pulley 353 and the cable 315 to freely rotate with respect to each other about an axis coinciding with a vertical length of the cable 315 proximate the swivel 354.

Figure 4:
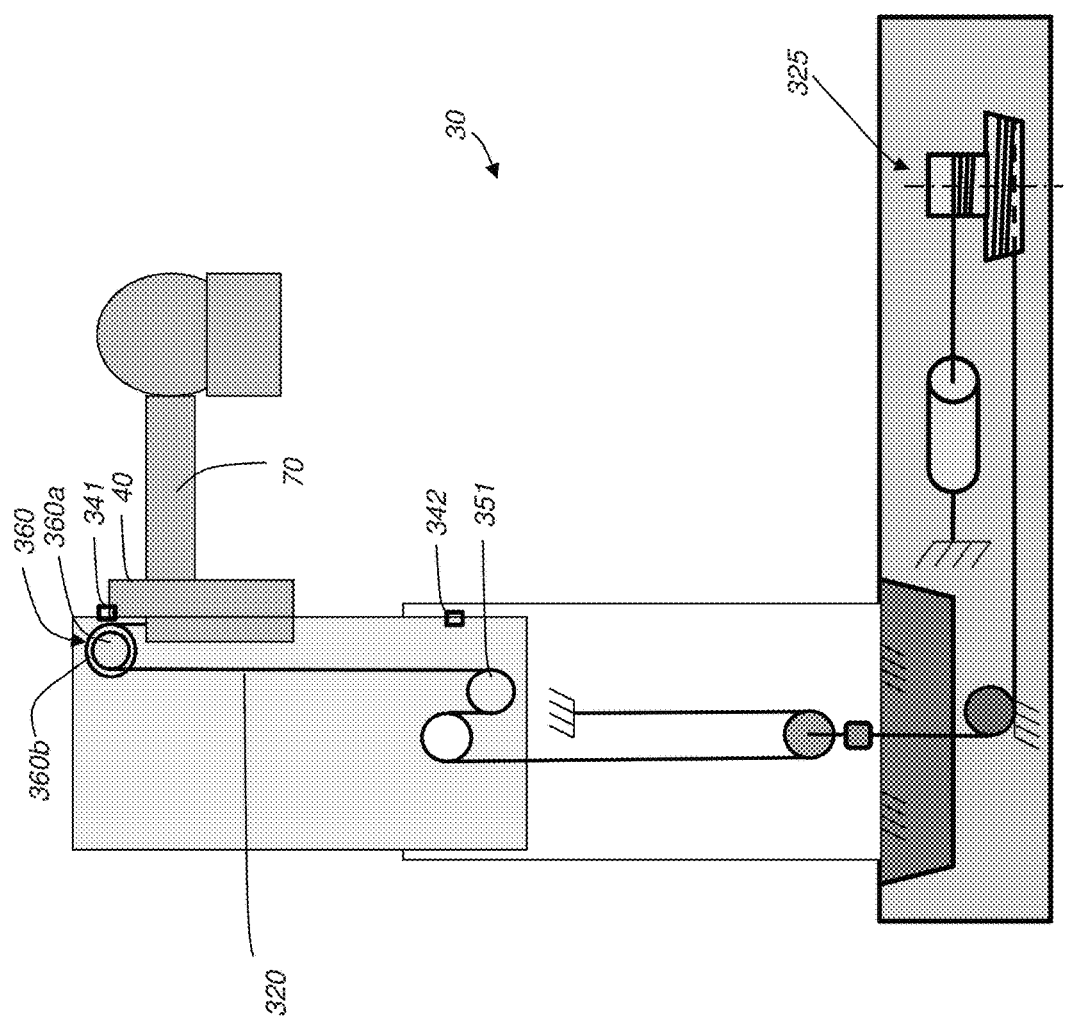
FIG. 4 is a schematic block diagram of a boom apparatus on a portion of a sectioned vertical column using another novel assembly of cables, pulleys, and spring to assist vertical positioning.

An alternative embodiment to the mechanical assist assembly described herein above is illustrated in the schematic diagram of FIG. 4, wherein a mechanical assist assembly is disposed within the vertical column 30 and within a housing of the transport frame 22 as described above in relation to the embodiment of FIG. 3, except that the third cable and pulley system, comprising counterweight 306, cable 305, fixed pulley 310, and cable ground 307 (all shown in FIG. 3), is not included, and a dual-radius (non-tapered) fixed pulley 360, having small radius portion 360a and larger radius portion 360b, replaces fixed pulley 350 (FIG. 3). For ease of reference, not all the elements of FIG. 4 are labeled with numerals, however, operation and structure of relevant elements are described with reference to FIG. 3 herein above. As explained herein above with respect to tapered dual radius fixed pulley 325 of FIG. 3, the dual radius fixed pulley 360 may also be configured as a single continuous cable or a two cable section pulley. In a two cable section embodiment, a cable, such as the section of cable 320 that extends to dual radius pulley 360 from pulley 351, may loop around and be anchored to the smaller radius portion 360a of the fixed dual radius pulley 360, and a second separate portion of cable 320 may extend from its attachment to the boom transport mechanism 40 and loop around and be anchored to the larger radius portion 360b of the dual radius fixed pulley 360. In a single cable embodiment, one continuous cable 320 loops around both the smaller and larger radius portions, 360a and 360b, respectively, of the dual radius fixed pulley 360. The single cable embodiment typically requires the cable 320 to be clamped, or anchored, to the dual radius fixed pulley 360 at a selected location between the two pulley radii. The portion of cable 320 looping around the smaller radius portion 360a of dual-radius fixed pulley 360 travels downward and around fixed pulley 351, as it does in the embodiment of FIG. 3, and the portion of cable 320 looping around the larger radius portion 360b of dual-radius fixed pulley 360 travels downward and is attached to the boom transport mechanism 40, as it does in the embodiment of FIG. 3.

Exemplary vertical movement of the boom 70, using the mechanical assist assemblies described herein, will now be briefly described. In the embodiments of the present invention as illustrated in FIGS. 3-4, the movement of the boom 70, relative to the movable column section 36, and the movement of the movable column section 36, relative to the stationary column section 32, are the same. In the embodiment of FIG. 3, the counterweight 306 is selectively weighted, or sized, to balance the movable column section 36. With respect to boom 70 and movable column section 36 movement, as the boom 70 is manually raised by an operator the movable column section 36 moves together with the boom 70 until eventually the movable column section 36 reaches a maximum height in its movement along stationary column section 32, whereby further upward urging of the boom 70 by the operator then causes the boom 70 to move upward within, and relative to, movable column section 36, but only if the boom 70 is not already at its maximum height along the movable column section 36, until boom 70 reaches its maximum height along movable column section 36. The balancing force provided by counterweight 306 assists in easing the force required from the operator to raise the movable column section 36 in this manner. The balancing force provided by counterweight 306 also assists in preventing downward freeplay (falling) movement of the movable column section 36 due to gravity.

As the boom 70 is manually lowered by an operator the movable column section 36 moves together with the boom 70 until eventually the movable column section 36 reaches a minimum height in its movement along stationary column section 32, whereby further downward urging of the boom 70 by the operator then causes the boom 70 to move downward within, and relative to, movable column section 36, but only if the boom 70 is not already at its minimum height along the movable column section 36, until boom 70 reaches its minimum height along movable column section 36. The balancing force provided by counterweight 306 assists in easing the force required from the operator to lower the movable column section 36 in this manner. The balancing force provided by counterweight 306 assists in preventing the movable column section 36 from free falling, due to gravity, after a manual downward urging from the operator in this manner.

In one embodiment, upper and lower latches, 341, 342, respectively, may be provided by attaching them to the movable column section 36 as shown in FIGS. 3-4. These latches 341, 342, may be configured to be manually engageable and releasable by the operator, or they may be electromechanically programmably controlled. The upper latch 341, when engaged to the boom 70, locks the boom 70 at its highest point of movement along movable column section 36, whereby upward or downward urging of the boom 70 by the operator causes the movable column section 36 to move upward or downward, respectively, between its maximum and minimum heights along the stationary column section 32, while the boom 70 remains stationary relative to the movable column section 36. The lower latch 342, when engaged to the boom 70, locks the boom 70 at its lowest point of movement along movable column section 36, whereby upward or downward urging of the boom 70 by the operator causes the movable column section 36 to move upward or downward, respectively, between its maximum and minimum heights along the stationary column section 32, while the boom 70 remains stationary relative to the movable column section 36. When the mobile radiography unit 20 is collapsed into a docked position for transport, or is being maneuvered into the docked position, such as shown in FIG. 2, the boom 70 is typically latched at the top of movable column section 36 using latch 341.

As the boom 70 is manually urged downward, the movable floating pulley 353 travels upward and the tension adjustment member 316, such as a spring, is stretched, or elongated. As the boom 70 is manually urged upward, the movable floating pulley 353 travels downward and the tension adjustment member 316, such as a spring, is shortened. The larger tapered radius portion 325b of the tapered dual radius fixed pulley 325 counteracts the increased tension exerted by the tension adjustment member 316, as it is elongated, so as to maintain, as much as possible, a constant tension force transmitted through cable 315 to floating movable pulley 353 in order to balance the weight of the boom 70 as it moves along the movable column section 36. The constant tension maintenance through cable 315 is achieved by unwinding cable 315 at an increasing radius from around the tapered radius portion 325b as the tension adjustment member 316 is elongated, and winding cable 315 at a decreasing radius around the tapered radius portion 325b as the tension adjustment member 316 is shortened. The size of the tension adjustment member 316, and thereby the force it exerts on cable 315, as well as the radial dimensions of the tapered dual radius fixed pulley 325 may be selectively designed according to the overall weights and dimensions of the operable components of the mobile radiography system as described herein.

Figure 5:
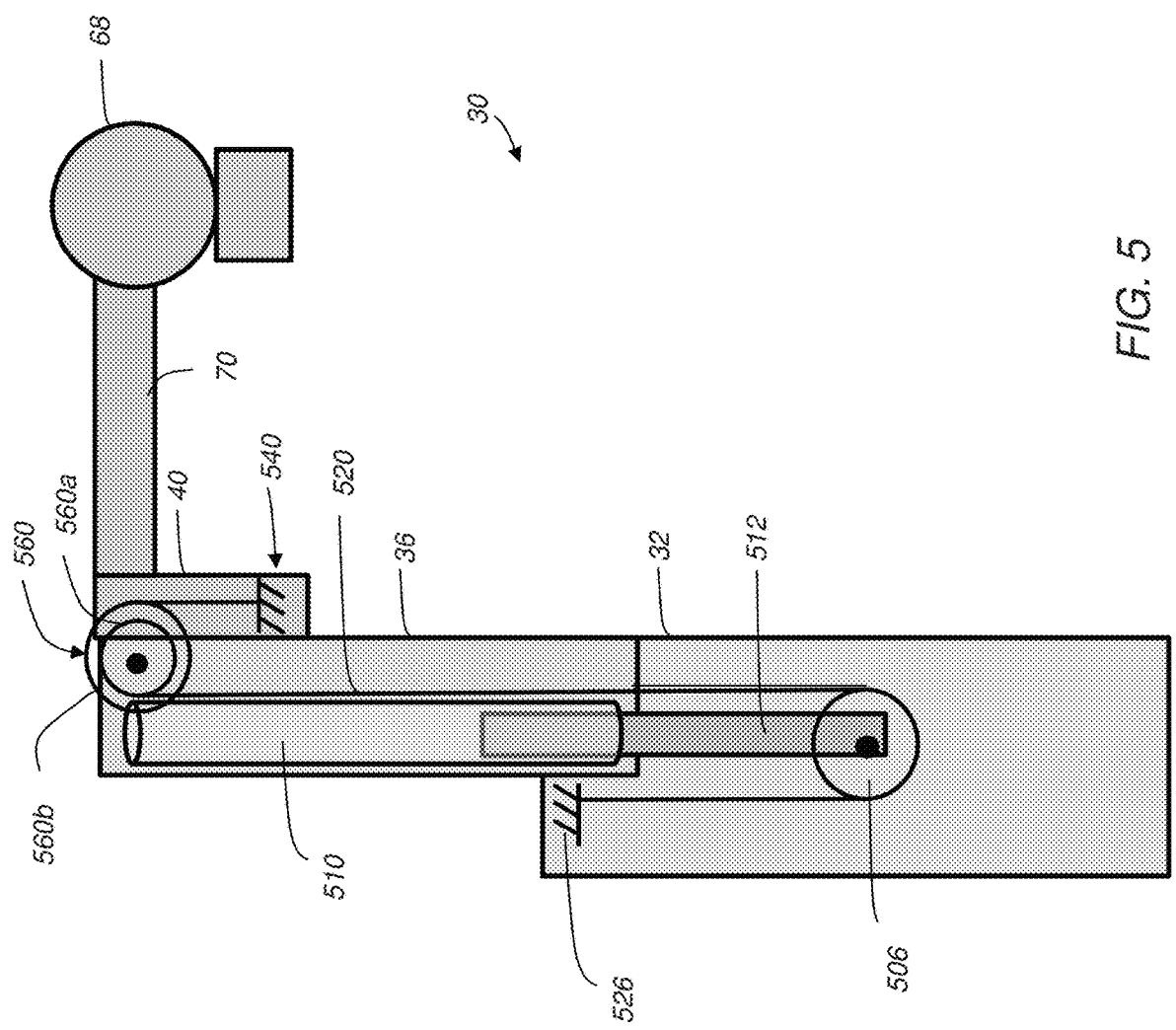
FIG. 5 is a schematic block diagram of a boom apparatus on a portion of a sectioned vertical column using a novel assembly of cables, pulleys and other components entirely disposed within or attached to, the movable section of the vertical column with only an anchor and attached cable in the base section of the vertical column.

FIG. 5 is a schematic diagram illustrating a vertical movement mechanical assist assembly which is mostly disposed in or on the movable column section 36 but for a cable anchor 526 attached to an interior surface of the base section 32. A cable 520 extends downward from the anchor point 526, attached to an interior surface of base section 32, and loops around a primary lifting pulley 506 attached to an end of a rigid arm 512 that is extendable vertically downward relative to, and from, the movable section 36 of the vertical column 30. Cable 520 extends upward from primary lifting pulley 506 and loops around a small radius portion 560a of dual radius pulley 560 (non-tapered). Cable 520 extends from a large radius portion 560b of dual radius pulley 560 down to the cable attachment point 540 at the boom transport mechanism 40. Dual radius pulley 560 is attached to an interior surface of the movable section 36, and has a smaller radius portion 560a and a larger radius portion 560b operating in a manner similar to the dual radius pulley 360 of FIG. 4, including the alternative attachment thereto of a single or two-section cable 520. The dual radius pulleys described herein are formed as unitary components that rotate together uniformly. The rigid arm 512 is variably extendable from a housing 510 that is fixedly attached within and to the movable section 36 of the vertical column 30. The rigid arm 512 may be variably extendable using a spring member, or using a motor control, which motor control may be pneumatic, hydraulic, or use a rotating threaded lead screw. The ratio of the smaller and larger radii of the dual radius fixed pulley 560 may be determined by the ratio of the total mass of the components mounted on the movable section 36 to the mass of the components mounted on the boom transport mechanism 40.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The invention claimed is:

1. A mobile radiography system comprising:
   a transport frame having wheels attached thereto for rollably transporting the system, the transport frame having a housing to enclose at least a portion of the system;
   a sectioned vertical column mounted on the transport frame about a vertical axis, the sectioned vertical column comprising:
      a base section supported by and attached to the transport frame, the base section remaining vertically stationary with respect to the vertical axis;
      a movable upper section, coupled to the base section, that is movable parallel to the vertical axis relative to the base section;
      a boom having a first boom end movably attached to the movable upper section and extending transversely therefrom, the boom further having an x-ray source attached to a second boom end thereof opposite the first boom end, the boom configured to move parallel to the vertical axis and relative to the movable upper section; and
      a column cable and pulley system comprising a column cable having a first column cable end attached to the first boom end and a second column cable end attached to a base section anchor in the base section; and
   the transport frame comprising:
      a transport frame cable and pulley system comprising a transport frame cable having a first transport frame cable end attached to a floating pulley supported by the column cable and a second transport frame cable end attached to a transport frame anchor in the transport frame.

2. The system of claim 1, wherein the transport frame cable comprises a spring disposed within the transport frame.

3. The system of claim 2, further comprising a dual radius pulley disposed within the transport frame, the dual radius pulley comprising a variable radius tapered portion and a constant radius portion, the constant radius portion having a smaller radial dimension than the variable radius tapered portion, and wherein the transport frame cable is looped around the dual radius pulley.

4. A support system comprising:
a wheeled transport frame having a vertical column attached thereto, the vertical column comprising:
a stationary base section attached to the wheeled transport frame, the stationary base section fixed in position relative to a vertical dimension, the stationary base section comprising a base section anchor;
a movable upper section attached to the stationary base section, the movable upper section movable vertically along the vertical dimension with respect to the stationary base section;
a support arm attached to the movable upper section, the support arm movable vertically with respect to the movable upper section; and
a column cable and pulley system comprising a column cable having a first cable end attached to the support arm and a second cable end attached to the base section anchor; and
the wheeled transport frame comprising a transport frame cable and pulley system comprising a transport frame cable having a first transport frame cable end attached to a floating pulley supported by the column cable and a second transport frame cable end attached to a transport frame anchor in the transport frame.

5. The system of claim 4, wherein the transport frame cable comprises a spring disposed within the transport frame.

6. The system of claim 5, further comprising a dual radius pulley disposed within the transport frame, the dual radius pulley comprising a variable radius tapered portion and a constant radius portion, the constant radius portion having a smaller radial dimension than the variable radius tapered portion, and wherein the transport frame cable is looped around the dual radius pulley.

7. A mobile radiography apparatus comprising:
a portable transport frame having wheels attached thereto for transporting the apparatus, the portable transport frame enclosing a frame anchor, a plurality of frame pulleys, and a frame cable comprising a first frame cable end attached to the frame anchor, the frame cable looping around each of the plurality of frame pulleys;
a stationary base section attached to the portable transport frame, the stationary base section fixed in a vertical position relative to the portable transport frame, the stationary base section comprising a base station anchor;
a movable upper section attached to the stationary base section, the movable upper section movable vertically with respect to the stationary base section;
a support arm attached to the movable upper section, the support arm movable vertically with respect to the movable upper section;
a plurality of column pulleys; and
a column cable having a first column cable end attached to the support arm and a second column cable end attached to the base section anchor, wherein the column cable is looped around each of the plurality of column pulleys, and wherein the frame cable comprises a second frame cable end attached to one of the plurality of column pulleys.

8. The apparatus of claim 7, wherein the plurality of column pulleys comprises:
a first column pulley attached to the movable upper section closer to a top edge thereof than to a bottom edge thereof;
a second column pulley attached to the movable upper section closer to the bottom edge thereof than to the top edge thereof;
a third column pulley attached to the stationary base section; and
a fourth floating pulley.

9. The apparatus of claim 8, wherein the column cable extends from the support arm upward to the first column pulley, the column cable loops around the first column pulley and extends downward to the second column pulley, the column cable loops around the second column pulley and extends upward to the third column pulley, and wherein the column cable loops around the third column pulley and extends downward to loop around the fourth floating pulley.

10. The apparatus of claim 9, wherein the plurality of frame pulleys comprises:
a first frame pulley attached to the portable transport frame, the first frame pulley having a first axis of rotation; and
a second frame pulley attached to the portable transport frame, the second frame pulley having a second axis of rotation transverse to the first axis of rotation.

11. The apparatus of claim 10, wherein the portable transport frame further comprises a tension adjustment member, the frame cable is attached to the tension adjustment member, the second frame cable end is attached to the fourth floating pulley, the frame cable loops around the first frame pulley and extends to the second frame pulley, and wherein the frame cable loops around the second frame pulley and extends to the tension adjustment member.

12. The apparatus of claim 11, wherein the second frame pulley comprises a dual radius tapering pulley having a tapering large pulley portion and a small pulley portion, the tapering large pulley portion having a diameter greater than the small pulley portion, the frame cable extends from the fourth floating pulley to the tapering large pulley portion of the second frame pulley, the frame cable loops around the tapering large pulley portion, the frame cable loops around the small pulley portion, and wherein the frame cable extends from the small pulley portion of the second frame pulley to the tension adjustment member.

13. The apparatus of claim 10, further comprising:
a counterweight;
a counterweight pulley; and
a counterweight cable having a first counterweight cable end attached to the counterweight and a second counterweight cable end attached to an anchor point on the movable upper section.

14. The apparatus of claim 13, wherein the counterweight cable extends from the counterweight upward to the counterweight pulley, the counterweight cable loops around the counterweight pulley and extends downward to the anchor point on the movable upper section.

15. The apparatus of claim 9, wherein the column cable does not extend below a bottom of the stationary base section.

16. The apparatus of claim 8, wherein the first column pulley comprises a dual radius column pulley having a wide pulley portion and a narrow pulley portion.

17. The apparatus of claim 16, wherein the column cable extends from the support arm upward to the wide pulley portion of the first column pulley, the column cable loops around the wide pulley portion, the column cable loops around the narrow pulley portion, and wherein the column cable extends downward from the narrow pulley portion of the first column pulley to the second column pulley.

18. The apparatus of claim 7, wherein the frame cable comprises a spring disposed within the portable transport frame.

19. The apparatus of claim 18, further comprising a dual radius pulley disposed within the portable transport frame, the dual radius pulley comprising a variable radius tapered portion and a constant radius portion, the constant radius portion having a smaller radial dimension than the variable radius tapered portion, and wherein the frame cable is looped around the dual radius pulley.

* * * * *